United States Patent [19]

Tummes et al.

[11] 4,138,588

[45] Feb. 6, 1979

[54] PROCESS FOR THE IMPROVED MANUFACTURE OF 2-ETHYLHEXANOL

[75] Inventors: Hans Tummes; Heinz Noeske, both of Oberhausen; Boy Cornils, Dinslaken; Waldemar Kascha, Oberhausen, all of Fed. Rep. of Germany

[73] Assignee: Ruhrchemie Aktiengesellschaft, Oberhausen, Fed. Rep. of Germany

[21] Appl. No.: 888,709

[22] Filed: Mar. 20, 1978

[30] Foreign Application Priority Data

Mar. 26, 1977 [DE] Fed. Rep. of Germany ....... 2713434

[51] Int. Cl.$^2$ ............................................. C07C 29/14
[52] U.S. Cl. .................................... 568/881; 568/913; 568/914
[58] Field of Search ................ 568/881, 913, 883, 914

[56] References Cited

U.S. PATENT DOCUMENTS

| 2,595,096 | 4/1952 | Parker | 568/914 |
| 2,614,128 | 10/1952 | Mertzweiller | 568/914 |
| 2,671,119 | 3/1954 | Mertzweiller | 568/883 |
| 3,501,537 | 3/1970 | Johnson, Jr. et al. | 568/913 |
| 3,935,285 | 1/1976 | Tummes et al. | 568/914 |

FOREIGN PATENT DOCUMENTS 672635 5/1952 United Kingdom ..................... 568/882

*Primary Examiner*—Joseph E. Evans
*Attorney, Agent, or Firm*—Sprung, Felfe, Horn, Lynch & Kramer

[57] ABSTRACT

An improvement in a process for the manufacture of 2-ethylhexanol wherein n-butyraldehyde is subjected to aldol condensation, the resultant aldol condensation product is catalytically hydrogenated in a hydrogenation stage and the hydrogenation product is subjected to two separate multiple stage distillations to separate, in the first case the first runnings, a fraction containing the main amount of 2-ethylhexanol, and the residue. In the second case this residue is separated into a 2-ethylhexanol fraction and a distillation residue, the improvement residing in cracking the distillation residue by heating the same at 200 to 250° C whereby to obtain cracked products comprising n-butanal, 2-ethylhexenal, 2-ethylhexanal, and/or 2-ethylhexanol together with non-cracked higher boiling substances. The cracked products are separated from the non-cracked products and the cracked products are recycled to the hydrogenation stage.

4 Claims, No Drawings

PROCESS FOR THE IMPROVED MANUFACTURE OF 2-ETHYLHEXANOL

BACKGROUND OF THE INVENTION

1. Field of the Invention

This relates to the manufacture of 2-ethylhexanol. More particularly this invention relates to the manufacture of 2-ethylhexanol by aldol condensation of n-butyraldehyde, hydrogenation of the condensation product and recovery of 2-ethylhexanol in a multi-stage distillation workup from the hydrogenation product. The invention resides in the cracking of the distillation residue whereby to obtain cracked products, which can be beneficially hydrogenated in the hydrogenation stage and thus converted into additional 2-ethylhexanol.

2. Discussion of the Prior Art

2-Ethylhexanol is used in large quantities for the manufacture of dioctyl phthalate, the favored plastiziser for PVC. The synthesis and purification of the alcohol are carried out in three stages.

In the first stage of the known process, (c.f. Chemie-Ingenieur-Technik, 41, 1969, No. 17, p. 976) n-butyraldehyde is brought into intimate contact with an aqueous sodium hydroxide solution at an elevated temperature. The n-butyraldehyde is thereby converted into 2-ethylhexenal via aldolization and simultaneous cleavage of water. The applied temperatures should lie between 90° and 130° C. and the concentration of the sodium hydroxide solution should be between 1 to 5%. 2-Ethylhexenal, being insoluble in water, forms, together with the small amount of by-products produced, an upper layer in the aqueous alkaline solution which can be readily separted.

The following composition is typical of the product from this reaction stage:
95.0% 2-Ethylhexenal
0.5% 2-Ethylhexanal
0.1% 2-Ethylhexanol
1.4% n-Butyraldehyde (monomer and trimer)
3.0% higher condensation products In the second stage, 2-ethylhexenal and 2-ethylhexanal are hydrogenated to 2-ethylhexanol, while n-butyraldehyde and portions of the trimeric n-butyraldehyde are hydrogenated to n-butanol. The higher condensation products containing the carbonyl group are hydrogenated to higher boiling compounds containing the hydroxyl group. The hydrogenation can take place with fixed bed hydrogenation catalysts in the liquid or gas phase. The pressures applied lie in the region of 20 to 200 bar for the liquid phase and generally between 2 to 10 bar for the gas phase. The temperatures employed are between 100° and 180° C.

Heptane occurs as by-product in very limited amounts, from the hydrogenation via decarbonylation of 2-ethylhexenal and 2-ethylhexanal. The recovery of pure 2-ethylhexanol in the third stage occurs distillatively via the separation of a fraction of the first runnings by means of a first running column and separation of a distillation residue in a main product column. Although the separation of the components with boiling points below that of 2-ethylhexanol can take place at normal or slightly reduced pressure, industrially, due to the high boiling point of 2-ethylhexanol, the entire distillation is carried out at a reduced pressure of 50 to 200 torr. However, it is not possible under these conditions to separate 2-ethylhexanol completely from the higher boiling components in the main product column. The bottom product of the main product column must therefore be redistilled in a further column, the last runnings column, in order to separate the 2-ethylhexanol in the residue from the higher boiling components. A temperature below 180° C. is usually maintained in the bottom product with this distillation (last runnings distillation). At the head of the column, the remaining 2-ethylhexanol is obtained together with small amounts of the higher boiling substances as a last runnings fraction. This is recycled to the hydrogenation or distillation and is thereby subjected to a further distillation, so that finally, 2-ethylhexanol is almost completely separated from the higher boiling substances, which are removed at the bottom of the last runnings column. They consist of the reaction products of 2-ethylhexenal with itself or with n-butyraldehyde and constitute oxygen-containing compounds with more than 8 carbon atoms. The boiling points of the reaction products lie above that of 2-ethylhexanol.

The manufacture of 2-ethylhexanol takes place with very high yield. In the aldolization stage, relative to n-butyraldehyde, a conversion of over 98% and a selectivity of over 97% is obtained and in the hydrogenation stage a conversion of 100% and a selectivity of over 99% is reached. The possibility of directly increasing the yield of value products by improving the selectivity, within the framework of the present process, is therefore very limited.

However, attempts are still being made to further increase the yield of 2-ethylhexanol, as even minor improvements can result in significant economic benefits due to the large quantities in which 2-ethylhexanol is manufactured.

It is an object of this invention, therefore, to improve the yield of 2-ethylhexanol whereby to provide such significant economic benefits. It is a further object of this invention to increase the 2-ethylhexanol yield without an accompanying large expense and to thereby provide an improved, commercially feasible, and economic process for the realization of large quantities of 2-ethylhexanol. It is a further object of this invention to improve the yield of 2-ethylhexanol by converting the distillation residue, normally obtained in the manufacture of 2-ethylhexanol, into products which can be hydrogenated in the hydrogenation stage to form additional 2-ethylhexanol.

SUMMARY OF THE INVENTION

Broadly this invention contemplates an improvement in a process for the manufacture of 2-ethylhexanol wherein n-butyraldehyde is subjected to aldol condensation, the resultant aldol condensation product is catalytically hydrogenated in a hydrogenation stage and the hydrogenation product is subjected to two separate multi-stage distillations to separate, in the first case the first runnings, a fraction containing the main amount of 2-ethylhexanol and the residue, in the second case this residue is separated into a 2-ethylhexanol fraction and a distillation residue, the improvement residing in cracking the distillation residue by heating the same at 200° to 250° C. whereby to obtain cracked products comprising n-butanal, 2-ethylhexenal, 2-ethylhexanal and/or 2-ethylhexanol together with non-cracked higher boiling substances, separating said cracked products from said non-cracked products and recycling said cracked products to said hydrogenation stage.

The cracking of the distillation residue which results from the distillation from the last runnings column can be performed thermally or catalytically although it is preferred to perform the same thermally. Generally speaking, the cracking of the residue is a partial cracking whereby to obtain n-butanal, 2-ethylhexenal, 2-ethylhexanal and/or 2-ethylhexanol as cracked products.

The process of the invention is conducted by performing the known aldol condensation of n-butyraldehyde employing sodium hydroxide, for instance, as catalyst. Aldol condensation product is then subjected to catalytic hydrogenation preferably performed in the vapor phase. The hydrogenation product is then subjected to a multi-stage distillation wherein in a first distillation column a first runnings is taken overhead which runnings comprise 2-ethylhexanol product. The bottoms from the distillation are then fed into a second distillation column from which most of the 2-ethylhexanol product is taken overhead. The bottoms from the second distillation column are then fed into a third distillation column also known as a last runnings column whereby last runnings are taken overhead, these last runnings comprising additional 2-ethylhexanol product. There results in the sump of the distillation column a distillation residue which is cracked in accordance with the invention.

The thermal treatment can be carried out at normal or reduced pressure. In order to prevent an enrichment of the higher boiling substances with boiling points above that of 2-ethylhexanol arising from the reintroduction of the cracked products to the hydrogenation stage, the products of the thermal cracking must be worked up distillatively into the required $C_4$ (n-butanal) and $C_8$ (2-ethylhexenal, 2-ethylhexanal, 2-ethylhexanol) products as well as into the non-converted higher boiling substances.

The cracking of the higher boiling substances is carried out expediently by a version of the process according to the invention. This requires that a temperature of 200° to 250° C. be present at the bottom of the last runnings column. Under these conditions the 2-ethylhexanal, present in the last runnings, and the cracked products are distilled over together. With this operation of the new procedure, non-cracked higher boiling products are also distilled over to a certain extent. It is therefore necessary to separate the distillate in a separate column, into a fraction consisting of n-butanal, 2-ethylhexenal, 2-ethylhexanal and 2-ethylhexanol and the residue consisting of the higher boiling substances.

The cracking of the higher boiling substances can take place in a separate stage after 2-ethylhexenal has been distilled over. The product of the thermal cracking has then to be distillatively separated.

Cracked products and non-cracked higher boiling substances can be separated in the column used for the cracking. The products, which have boiling points above that of 2-ethylhexanol, are removed as vapor via a side outlet just above the bottom. At the head of the column the products, with boiling points up to that of 2-ethylhexanol, are separated off and recycled to the hydrogenation stage of the aldolization product.

In order to more fully illustrate the nature of the invention in a manner of practicing the same the following examples are presented:

EXAMPLE 1 n-Butyraldehyde was added to an approx. 3% aqueous sodium hydroxide solution with a ratio of 9 parts by weight sodium hydroxide solution to 1 part by weight aldehyde, and intensively mixed at a temperature of 100° to 130° C. 2-Ethylhexenal, which was formed by cleavage of water, was then hydrogenated with a fixed bed nickel catalyst in the gas phase at approx. 110° C. The hydrogenation product had the following composition:
1.7 parts by weight n-Butanol
0.6 parts by weight Heptane
0.01 parts by weight 2-Ethylhexanal
94.69 parts by weight 2-Ethylhexanol
3.0 parts by weight higher boiling substances The usual industrial distillative separation was conducted in three stages under the following conditions:

|  | First runnings column | Main product column | Last runnings column |
| --- | --- | --- | --- |
| Head Temperature (° C) | 80 | 125 | 113 |
| Bottom Temperature (° C) | 158 | 152 | 158 |
| Pressure (mbar) | 180 | 133 | 105 |
| Reflux | 5 : 1 | 0.85 : 1 | 0.6 : 1 |

The following was obtained from 100 parts by weight of hydrogenation product:
2.3 parts by weight first runnings, including
1.7 parts by weight n-butanol
94.7 parts by weight 2-ethylhexanol (99.7%)
3.0 parts by weight higher boiling substances If the resulting 3 parts by weight of higher boiling substances from the last runnings column are distilled in a connected, continuously operated, column in such a way, that a bottom temperature of 230° C. is maintained, then 1.5 parts by weight (corresponding to 50% of the added higher boiling substances) pass over the head of the column. The cracked distillate had the following composition:
24.3 parts by weight n-Butyraldehyde
1.8 parts by weight 2-Ethylhexanal
42.5 parts by weight 2-Ethylhexenal
8.5 parts by weight 2-Ethylhexanol
22.9 parts by weight higher boiling substances 1.5 parts by weight (i.e. 50% of the added higher boiling substances) remained at the bottom of the column. Via distillation in a column with 10 trays, the substances with boiling points up to and including 2-ethylhexanol, were separated from the cracked distillate and recycled to the hydrogenation of the aldolization product. The 2-ethylhexanol yield increased by 0.92 parts by weight for each 100 parts by weight of the hydrogenation product and the n-butanol yield by 0.36 parts by weight, while the higher boiling substances were reduced by 36.7% from 3 parts by weight to 1.9 parts by weight.

EXAMPLE 2

According to the procedure used in Example 1 an aldolization product, after the treatment of butyraldehyde with an aqueous sodium hydroxide solution, had the following composition:
1.5 parts by weight n-Butyraldehyde
0.5 parts by weight 2-Ethylhexanal
94.9 parts by weight 2-Ethylhexenal
0.1 parts by weight 2-Ethylhexanol
3.0 parts by weight higher boiling substances 100 parts by weight of this product were introduced into an evaporator and were evaporated in the presence of hydrogen until 6 parts by weight remained as residue in the evaporator. They were then led, in vapor form, over a fixed bed nickel hydrogenation catalyst at a temperature of about 110° C. In order that complete hydrogenation took place, the resulting hydrogenation product was reacted in the liquid phase with a fixed bed nickel catalyst in a connected hydrogenation tube. It was then distilled under the same conditions and in the 3 stages as described in Example 1 and then worked up to pure 2-ethylhexanol. The 6 parts by weight residue in the evaportor from the gas phase hydrogenation were introduced into the last runnings column in order to separate the higher boiling substances. At the bottom of the last runnings column, 3.3 parts by weight distillation residue remained relative to 100 parts of the aldolization product employed. These were then continuously cracked and distilled in a connected 10 tray column with a bottom temperature of 230° C. which has a side outlet at the 3rd tray from the bottom. At the head, 1.6 parts by weight and at the side outlet 1.4 parts by weight higher boiling substances were distilled over, while 0.3 parts by weight remained as distillation residue (all figures relative to 100 parts by weight aldolization product). The head distillate had the following composition:

29.2 parts by weight n-Butyraldehyde
1.8 parts by weight 2-Ethylhexanal
50.5 parts by weight 2-Ethylhexenal
10.0 parts by weight 2-Ethylhexanol
8.5 parts by weight higher boiling substances It was then recycled to the liquid phase hydrogenation.

Corresponding to 100 parts by weight of aldolization product, the 2-ethylhexanol yield increased by 0.99 parts by weight and the n-butanol yield by 0.46 parts by weight compared to a procedure without the crack distillation.

What is claimed is:

1. In a process for the manufacture of 2-ethylhexanol wherein n-butyraldehyde is subjected to aldol condensation, the resultant aldol condensation product is catalytically hydrogenated in a hydrogenation stage and the hydrogenation product is subjected to two separate multiple stage distillations to separate, in the first case the first runnings, a fraction containing the main amount of 2-ethylhexanol, and the residue, in the second case this residue is separated into a 2-ethylhexanol fraction and a distillation residue, the improvement which comprises cracking said distillation residue by heating the same at 200° to 250° C. whereby to obtain cracked products comprising n-butanal, 2-ethylhexenal, 2-ethylhexanal, and/or 2-ethylhexanol together with non-cracked higher boiling substances, separating said cracked products from said non-cracked products and recycling said cracked products to said hydrogenation stage.

2. A process according to claim 1 wherein the cracking of said distillation residue is performed in the distillation vessel and the resultant cracked products taken overhead along with some non-cracked higher boiling products are separated from these non-cracked products in a separate column.

3. A process according to claim 1 wherein the cracking of said residue is carried out in a separate stage.

4. A process according to claim 1 wherein the cracking is performed in a distillation column whose bottom temperature is 220° to 250° C., vaporized products having a boiling point above that of 2-ethylhexanol are separated as a side cut immediately above the bottom of the distillation column and the products with boiling points up to that of 2-ethylhexanol are removed overhead and recycled to said hydrogenation stage.

* * * * *